United States Patent [19]
Peterson et al.

[11] Patent Number: 5,900,415
[45] Date of Patent: May 4, 1999

[54] CERTAIN SUBSTITUTED BENZYLAMINE DERIVATIVES; A NEW CLASS OF NEUROPEPTIDE Y1 SPECIFIC LIGANDS

[75] Inventors: John Matthew Peterson, New Haven; Charles Albert Blum; Guolin Cai, both of Guilford; Alan Jeffrey Hutchison, Madison, all of Conn.

[73] Assignee: Pfizer Inc., New York, N.Y.

[21] Appl. No.: 08/817,641

[22] PCT Filed: Nov. 7, 1995

[86] PCT No.: PCT/US95/14472

§ 371 Date: May 29, 1997

§ 102(e) Date: May 29, 1997

[87] PCT Pub. No.: WO96/14307

PCT Pub. Date: May 17, 1996

Related U.S. Application Data

[63] Continuation-in-part of application No. 08/478,383, Jun. 7, 1995, abandoned, and application No. 08/484,974, Jun. 7, 1995, abandoned, each is a continuation-in-part of application No.08/335,475, Nov. 7, 1994, abandoned.

[51] Int. Cl.[6] .................... A61K 31/495; C07D 295/096; C07D 407/04; C07D 409/04
[52] U.S. Cl. ..................... 514/252; 514/255; 544/295; 544/360; 544/374; 544/377; 544/379; 544/392; 544/393; 544/394; 544/364
[58] Field of Search ..................................... 544/295, 360, 544/374, 377, 393, 394, 364, 379, 392; 514/252, 255

[56] References Cited

U.S. PATENT DOCUMENTS

| | | | |
|---|---|---|---|
| 4,845,221 | 7/1989 | Stack et al. | 544/295 |
| 5,352,678 | 10/1994 | Mattson, et al. | 514/253 |
| 5,622,951 | 4/1997 | Ward et al. | 514/253 |

FOREIGN PATENT DOCUMENTS 0395312  10/1990  European Pat. Off.

OTHER PUBLICATIONS

Casy, A.F., et al. "Opioid Properties of Some Isomeric Derivatives of Phencyclidine", *J. Pharm. Pharmacol.*, 44, 19–23 (1992).

Woods, J., et al. "Evaluation of New Compounds for Opioid Activity", *NIDA Res. Monogr.*, 90, 421–467 (1988).

Aceto, M., et al. "Dependence Studies of New compounds in the Rhesus Monkey, Rat, and Mouse, 1987", *NIND Res. Monogr.*, 81, 485–542 (1988).

Itzhak, Y., et al. "Characterization of Specific Binding Sites for [$^3$H](d)–N–Allylnormetazocine in Rat Brain Membranes", *Mol. Pharm.*, 27, 46–52 (1984).

Itzhak, Y. et al., "A Novel Phencyclidine Analog Interacts Selectively with Mu Opioid Receptors", *J. Pharmocol. Exp. Ther.*, 230, 383–386 (1984).

Johnson, N. et al, "Interaction of Two Phencyclidine Opiate–like Derivatives with $^3$H–Opioid Binding Sites", *European Journal of Pharmacology*, 101, 281–284 (1984).

Itzhak, Y., et al., "Receptor Binding and Antinociceptive Properties of Phencyclidine Opiate–like Derivatives", *European Journal of Pharmacology*, 72, 305–311 (1981).

Itzhak, Y., et al., "New Analgesic Drugs Derived from Phencyclidine", *J. Med. Chem.*, 24, 496–499 (1981).

Aboul–Enein, M. N., et al., "Synthesis of Ethyl 1–(1–phenylcyclohexy)–4–phenylpiperidine–4–carboxylate as Potential Analgesic", *Sci. Pharm.*, 56, 207–210 (1988).

Roth, H. J., et al., Photocyclisierung von 3–Aminoketonen zu 2–Amino–cyclopropanolen–(1) und deren Isomerisierung, *Arch. Pharmaz.*, 307, 584–595 (1974).

Al–Deeb, O. A., et al., "Synthesis of New (1–Phenylcyclohexyl) Piperazine Derivatives as Potential Analgesics", *Bull. Fac. Pharm. Cairo Univ.*, vol. 31, No. 3, 475–479 (1993).

Registry of Toxic Effects of Chemical Substances by National Institute of Occupational Safety and Health (12/90).

Grundemar, L., et al., "Neuropeptide Y effector systems: perspectives for drug development", *TIPS Reviews*, 15, 153–159 (1994).

*Primary Examiner*—Emily Bernhardt
*Attorney, Agent, or Firm*—Peter C. Richardson; Gregg C. Benson; Mervin E. Brokke

[57] ABSTRACT

This invention encompasses compounds of formula (I) and the pharmaceutically

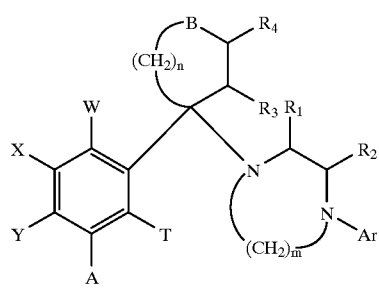

acceptable salts thereof, wherein W,X,Y,A,T,$R_1$–$R_4$,B,Ar,n and m are described herein and are useful in treating feeding disorders and certain cardiovascular diseases due to the binding of these compounds to human Neuropeptide Y1 receptors.

8 Claims, No Drawings

CERTAIN SUBSTITUTED BENZYLAMINE DERIVATIVES; A NEW CLASS OF NEUROPEPTIDE Y1 SPECIFIC LIGANDS

This application is the National Stage of International Application No. PCT/US95/14472 filed Nov. 7, 1995 which is a continuation-in-part of U.S. application Ser. No. 478,383 filed Jun. 7, 1995, now abandoned, which is a continuation-in-part of U.S. application Ser. No. 08/335,475 filed Nov. 7, 1994, now abandoned, and which (international application) is also a continuation-in-part of U.S. Ser. No. 08/484,974 filed Jun. 7, 1995, now abandoned, which is a continuation-in-part of U.S. Ser. No. 08/335,475 filed Nov. 7, 1994, now abandoned.

BACKGROUND OF THE INVENTION

1. Field of the Invention

This invention relates to certain substituted benzylamine derivatives which selectively bind to human Neuropeptide Y1 (NPY1) receptors. This invention also relates to pharmaceutical compositions comprising such compounds. It further relates to the use of such compounds and compositions in treating feeding disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of Neuropeptide $Y_1$ receptors is related to vasoconstriction, Wahlestedt et al., Regul. Peptides, 13: 307–318 (1986), McCauley and Westfall, J. Pharmacol. Exp. Ther. 261: 863–868 (1992), and Grundemar et al., Br. J. Pharmacol. 105: 45–50 (1992); and to stimulation of consummatory behavior, Flood and Morley, Peptides, 10: 963–966 (1989). Leibowitz and Alexander, Peptides, 12: 1251–1260 (1991), and Stanley et al., Peptides, 13: 581–587 (1992).

Grundemar and Hakanson, TiPS, May 1994 [Vol. 15], 153–159, state that, in animals, Neuropeptide Y is a powerful stimuli of food intake, and an inducer of vasoconstriction leading to hypertension. They further point out that low levels of Neuropeptide Y is associated with loss of appetite. These reports clearly indicate that compounds that inhibit the activity of this protein will reduce hypertension and appetite in animals.

SUMMARY OF THE INVENTION

Compounds that interact with NPY1 receptors and inhibit the activity of Neuropeptide Y at those receptors are useful in treating eating disorders such as, for example, obesity and bulimia, and certain cardiovascular diseases, such as, for example, hypertension.

This invention provides novel compounds of Formula I which selectively bind to Neuropeptide $Y_1$ (NPY1) receptors. Such compounds are useful in treating feeding disorders such as obesity and bulimia as well as certain cardiovascular diseases such as essential hypertension.

The invention also provides pharmaceutical compositions comprising compounds of Formula I. The invention thus further relates to the use of such compounds and compositions in the treatment of eating as well as certain cardiovascular diseases. Accordingly, a broad embodiment of the invention is directed to a compound of Formula I:

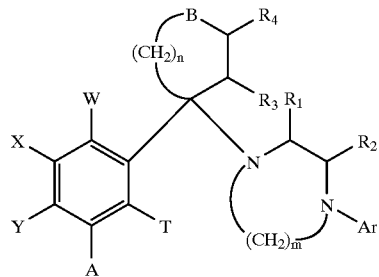

where
- Ar is an aryl group
- B is sulfur, oxygen, a substituted nitrogen atom, or a mono- or disubstituted carbon atom;
- n is 1,2, or 3;
- m is 2, 3, or 4;
- W, X, Y, and T are the same or different and represent hydrogen, halogen, hydroxy, straight or branched chain lower alkyl having 1–6 carbon atoms, or straight or branched chain lower alkoxy having 1–6 carbon atoms;
- $R_1$ and $R_2$ independently represent hydrogen, or straight or branched chain lower alkyl having 1–6 carbon atoms; and
- $R_3$ and $R_4$ are the same or different and represent hydrogen, straight or branched chain lower alkyl having 1–6 carbon atoms, or straight or branched chain lower alkoxy having 1–6 carbon atoms.

These compounds are highly selective partial agonists or antagonists at human NPY1 receptors and are useful in the diagnosis and treatment of feeding disorders such as obesity and bulimia as well as certain cardiovascular diseases such as essential hypertension and congestive heart failure.

DETAILED DESCRIPTION OF THE INVENTION

The novel compounds encompassed by the instant invention can be described by general formula I:

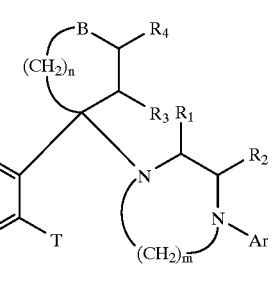

where
- Ar is an aryl group preferably selected from the group consisting of phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;
- B is sulfur, oxygen, $N(R_5)$ or $C(R_5)(R_6)$;
- n is 1, 2, or 3;
- m is 2, 3, or 4;
- W, X, Y, and T are the same or different and represent hydrogen, halogen, hydroxy, straight or branched chain lower alkyl having 1–6 carbon atoms, or straight or branched chain lower alkoxy having 1–6 carbon atoms;

$R_1$ and $R_2$ are the same or different and represent hydrogen, or straight or branched chain lower alkyl having 1–6 carbon atoms;

$R_3$ and $R_4$ are the same or different and represent hydrogen, straight or branched chain lower alkyl having 1–6 carbon atoms, or straight or branched chain lower alkoxy having 1–6 carbon atoms;

$R_5$ represents straight or branched chain lower alkyl having 1–6 carbon atoms, phenyl, 2-, 3-, or 4-pyridyl, or phenyl, 2-, 3-, or 4-pyridyl straight or branched chain lower alkyl having 1–6 carbon atoms; and A and $R_6$ are the same or different and represent
hydrogen, hydroxyl, amino, straight or branched chain lower alkyl having 1–6 carbon atoms, straight or branched chain lower alkoxy having 1–6 carbon atoms, phenyl, 2-, 3-, or 4-pyridyl, phenoxy, 2- 3-, or 4- pyridyloxy, or
—(CH$_2$)$_p$—A'—(CH$_2$)$_q$—B' where
p is 0–5, q is 1–5, and A' is a direct bond, oxygen or sulfur, and
B' is hydrogen, straight or branched chain lower alkyl having 1–6 carbon atoms, straight or branched chain lower alkoxy having 1–6 carbon atoms, phenyl, 2-, 3-, or 4-pyridyl, phenoxy, 2-, 3-, or 4-pyridyloxy, carboxyl, carboalkoxy, carboxamido, mono or dialkylcarboxamido, amino, or mono or dialkylamino.

Preferred compounds according to Formula I are those where Ar is optionally substituted phenyl, pyrimidinyl or pyridyl, B is carbon optionally substituted with phenyl or alkyl, and W, X, Y, A, T, and R1–$R_4$ are hydrogen. Particularly, preferred compounds or Formula I are those where Ar is phenyl, pyrimidinyl or pyridyl, B is carbon optionally substituted with phenyl or alkyl, and W, X, Y, A, T, and $R_1$–$R_4$ are hydrogen.

The invention also relates to compounds of formula IA:

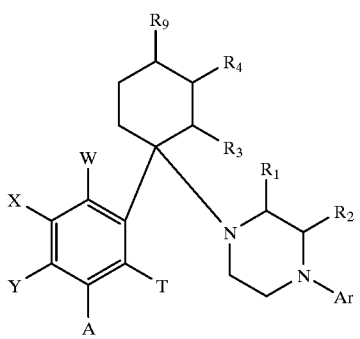

where
Ar is phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;
A, W, X, Y, and T are the same or different and represent hydrogen, halogen, hydroxy, straight or branched chain lower alkyl having 1–6 carbon atoms, or straight or branched chain lower alkoxy having 1–6 carbon atoms;
$R_1$ and $R_2$ are the same or different and represent hydrogen, or straight or branched chain lower alkyl having 1–6 carbon atoms;
$R_3$ and $R_4$ are the same or different and represent hydrogen, straight or branched chain lower all having 1–6 carbon atoms, or straight or branched chain lower alkoxy having 1–6 carbon atoms; and $R_9$ represents hydrogen, straight or branched chain lower alkyl having 1–6 carbon atoms, phenyl.

The invention further encompasses compounds of Formula II:

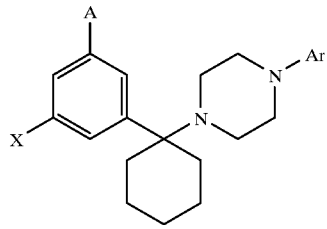

where A and X independently represent alkoxy and Ar represents phenyl, pyrimidinyl, or pyridyl.

Preferred compounds of Formula II are those where X and A are methoxy, ethoxy, isopropoxy, or butoxy, and Ar represents phenyl, pyrimidinyl, or pyridyl.

The invention further includes compounds of Formula III:

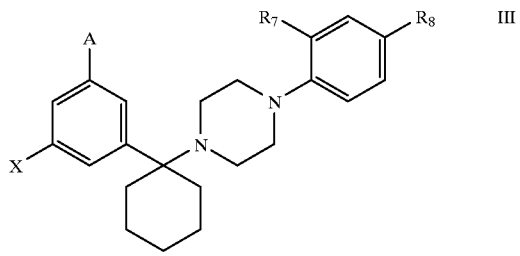

where X and A independently represent alkoxy and $R_7$ and $R_8$ are different and represent hydrogen or fluorine.

The invention further encompasses compounds of Formula IV:

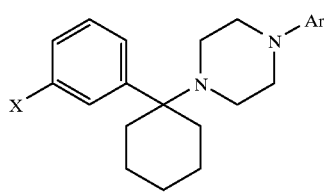

where X represents hydroxy and Ar represents phenyl, pyrimidinyl, or pyridyl.

The invention further encompasses compounds of Formula V:

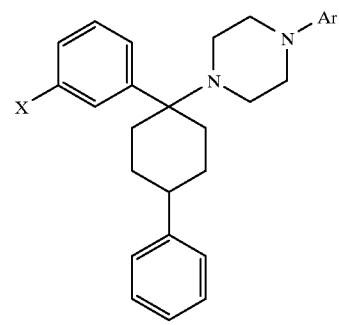

where X represents alkoxy and Ar represents phenyl, pyrimidinyl, or pyridyl.

Preferred compounds of Formula V are those where X is methoxy, ethoxy, isopropoxy, or butoxy, and Ar represents phenyl. Particularly preferred compounds of Formula V are those where X is methoxymethoxy or ethoxymethoxy.

The invention also includes compounds of Formula VI:

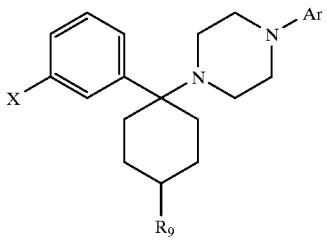

VI where X represents alkoxy, $R_9$ is alkyl, and Ar represents phenyl, pyrimidinyl, or pyridyl.

Preferred compounds of Formula VI are those where X is methoxy, ethoxy, isopropoxy, or butoxy, $R_9$ is alkyl, and Ar represents phenyl. Particularly preferred compounds of Formula VI are those where X is methoxy, ethoxy, isopropoxy, or butoxy, $R_9$ is methyl, and Ar represents phenyl. Other particularly preferred compounds of Formula VI are those where X is methoxymethoxy or ethoxymethoxy, $R_9$ is methyl, and Ar represents phenyl.

The invention also encompasses compounds of Formula VII:

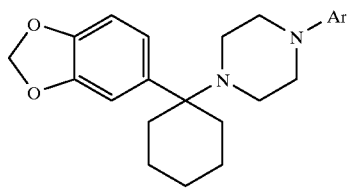

VII where Ar represents optionally substituted phenyl, pyrimidinyl, or pyridyl.

Preferred compounds of Formula Ar represents phenyl, pyrimidinyl, or pyridyl.

Representative compounds of the present invention, which are encompassed by Formula I–VII, include, but are not limited to the compounds in FIG. I and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The invention also relates to compounds of formula VIII:

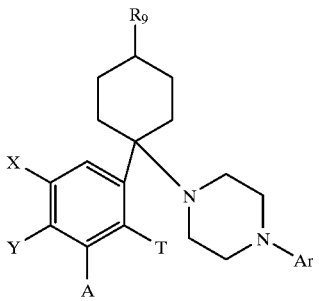

VIII where

Ar is phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;

A, X, Y, and T are the same or different and represent hydrogen, halogen, hydroxy, straight or branched chain lower alkyl having 1–6 carbon atoms, or straight or branched chain lower alkoxy having 1–6 carbon atoms; and $R_9$ represents hydrogen, straight or branched chain lower alkyl having 1–6 carbon atoms, or phenyl.

The present invention also encompasses the acylated prodrugs of the compounds of Formula I–VIII. Those skilled in the art will recognize various synthetic methodologies which may be employed to prepare non-toxic pharmaceutically acceptable addition salts and acylated prodrugs of the compounds encompassed by Formula I.

The invention encompasses both diasteriomers of the compounds having 1,4-substitution on the cyclohexane ring. I.e., the invention encompasses both cis-, and trans-1,4-cyclohexanes. Preferred compounds of the invention having 1,4-substitution on the cyclohexane ring are those where the nitrogen atom forming the piperazine ring and the alkyl or phenyl group in the 4-position of the cyclohexane ring are "cis" with respect to each other. Thus, preferred compounds of the invention having such substitution are those that are cis-1-piperazinyl-4-alkyl or phenyl-cyclohexanes.

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower all, lower alkoxy, lower alkylthio, trifluoromethyl, lower acyloxy, aryl, heteroaryl, and hydroxy.

By "alkyl" and "lower alkyl" is meant straight and branched chain alkyl groups having from 1–6 carbon atoms.

By "lower alkoxy" and "alkoxy" is meant straight and branched chain alkoxy groups having from 1–6 carbon atoms.

By "halogen" is meant fluorine, chlorine, bromine and iodine.

By 2-, 3-, and 4-pryidyloxy is meant groups of the following formulas respectively:

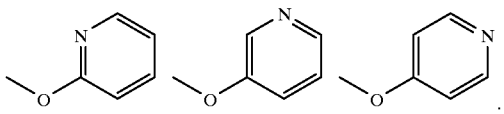

The pharmaceutical utility of compounds of this invention is indicated by the following assay for human NPY1 receptor activity.

Assay for Human NPY1 receptor binding activity

The procedure used is similar to that described by Gordon et al. (J. Neurochem. 55:506–513, 1990). SK-N-MC cells were purchased from ATCC (Rockville, Md.). Cells were maintained at 37° C. and 5% $CO_2$ in Dulbecco's modified essential media (DMEM) with L-glutamine and 110 mg/L sodium pyruvate, which was supplemented with 10% fetal bovine serum and 25 mM HEPES (pH 7.3). The binding assay was performed in 24-well plates (Falcon) when the cells were confluent. Taking care to not disturb the cells on the bottom of the wells, the media was aspirated, and 0.5 ml of Dulbecco's phosphate buffered saline (DPBS) with calcium and magnesium were added to each well. The DPBS was aspirated and an additional aliquot of DPBS was added and aspirated. To begin the assay, binding buffer consisting of serum-free DMEM containing 0.5% bovine serum albumin, 0.1% bacitracin and 0.1 mM phenylmethylsulfonylfluoride was added to each well. The cells and the binding buffer preincubated for 30 minutes at room temperature, at which point the drug dilution and [$^{125}$I]PYY (NEN-DuPont: 50000–75000 cpm–50 pM) were added to yield a final volume of 250 ul. Nonspecific binding was defined with 1 mM NPY (porcine or human, Bachem Calif.). After a 3 hour incubation at room temperature, the plates were then put on ice and the wells were aspirated. The cells were washed 4–6 times with 0.5 ml of ice-cold DPBS. A dilute solution of Triton X-100 (1%) was then added to each well. After approximately 1 hour at room temperature, an aliquot from each well was transferred to a 12×75 mm testtube, and the amount of [$^{125}$I] was quantitated on a gamma counter with an efficiency of 80–85% (Genesys 5000, Laboratory Technologies). IC$_{50}$ values were calculated with the non-linear curve fitting program RS/1 (BBN Software Products Corp., Cambridge, Mass.). The binding characteristics for compounds of this invention are shown in Table 1.

TABLE I

| Compound Number | IC$_{50}$ ($\mu$M) |
| --- | --- |
| 9 | 0.137 |
| 13 (cis isomer) | 0.067 |
| 18 (cis isomer) | 0.075 |
| 20 (cis isomer) | 0.076 |
| 21 (trans isomer) | 0.525 |
| 29 (cis isomer) | 0.039 |

Compounds 13, 18, 20 and 29 are particularly preferred embodiments of the present invention because of their potency in binding to human NPY1 receptors.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Scheme I. Those having skill in the art will recognize that the starting materials may be varied and additional steps employed to produce compounds encompassed by the present invention.

Scheme I

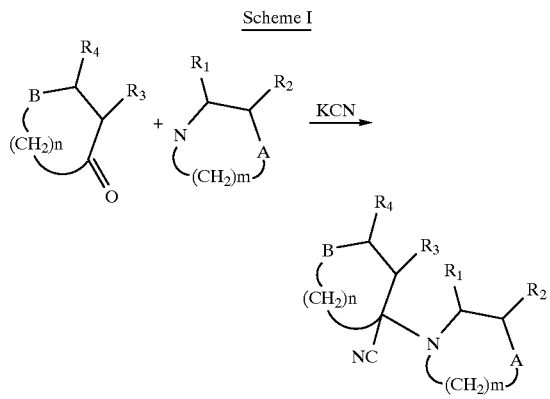

-continued

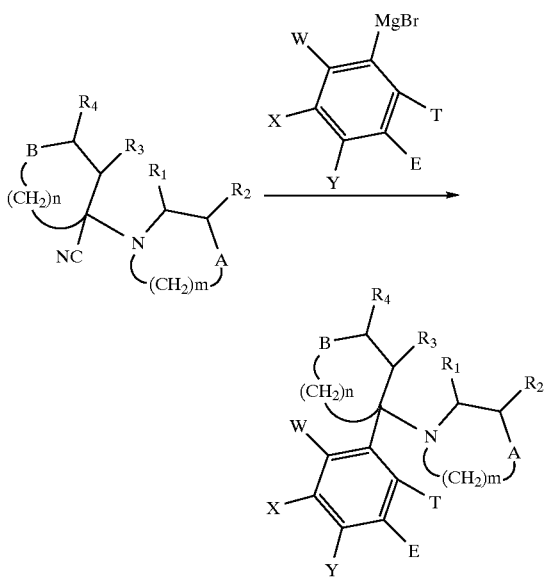

where
  A is ArN or ArCH where Ar is phenyl, 2, 3, or 4 pyridyl, 2 or 3 thienyl, 2, 4 or 5 pyrimidyl either unsubstituted or mono or disubstituted with halogen, hydroxy, or straight or branched chain lower alkyl having 1–6 carbon atoms;
  B is sulfur, oxygen $NR_5$ or $CR_5R_6$
  n is 1, 2, or 3;
  m is 2, 3, or 4;
  W, X, Y, Z, T are the same or different and represent hydrogen, halogen, hydroxy, straight or branched chain lower alkyl having 1–6 carbon atoms, or straight or branched chain lower alkoxy having 1–6 carbon atoms;
  $R_1$ and $R_2$ are the same or different and represent hydrogen, or straight or branched chain lower alkyl having 1–6 carbon atoms;
  $R_3$ and $R_4$ are the same or different and represent hydrogen, straight or branched chain lower alkyl having 1–6 carbon atoms, or straight or branched chain lower alkoxy having 1–6 carbon atoms;
  $R_5$ represents straight or branched chain lower alkyl having 1–6 carbon atoms, phenyl, 2, 3, or 4 pyridyl, or phenyl, 2, 3, or 4 pyridyl straight or branched chain lower alkyl having 1–6 carbon atoms;
  E and $R_6$ are the same or different and represent hydrogen, hydroxyl, amino, straight or branched chain lower alkyl having 1–6 carbon atoms, straight or branched chain lower alkoxy having 1–6 carbon atoms, phenyl, 2, 3, or 4 pyridyl, phenyloxy, 2, 3, or 4 pyridyloxy, or —$(CH_2)_p$—A'—$(CH_2)_q$—B' where p represents 0–5 and q represents 1–5 and A' is a direct bond, oxygen or sulfur and B' is hydrogen, straight or branched chain lower alkyl having 1–6 carbon atoms, straight or branched chain lower alkoxy having 1–6 carbon atoms, phenyl, 2, 3, or 4 pyridyl, phenyloxy, 2, 3, or 4 pyridyloxy, carboxyl, carboalkoxy, unsubstituted, mono or dialkylcarboxamido, amino, or mono or dialkylamino.

The invention is illustrated further by the following examples which are not to be construed as limiting the invention in scope or spirit to the specific procedures and compounds described in them.

EXAMPLE I

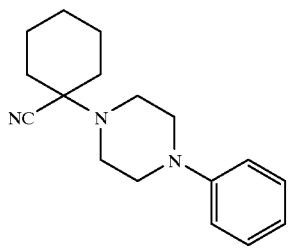

1-Phenylpiperazine (11.3 mL, 12 g, 75 mmol) was suspended in 100 mL water. The pH was adjusted to 3 using 10% HCl. Cyclohexanone (7.8 mL, 7.4 g, 75 mmol) was added followed by KCN (5 g, 75 mmol). The mixture was stirred 15 hours at room temperature during which time the product solidified. The product was collected by filtration, washed with water, then recrystallized from ethanol to give 14.5 g of 1-Cyano-1-(4-phenylpiperazin-1-yl)-cyclohexane as a white solid (73% yield), mp=133–135° C.

EXAMPLE II

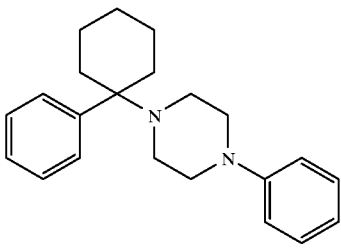

1-Cyano-1-(4-phenylpiperazin-1-yl)-cyclohexane (300 mg, 1.1 mmol) was dissolved in 10 mL ether under N2 at room temperature. Phenyl magnesium bromide (4 mL of a 3 M ether solution) was added and the reaction mixture stirred 15 hours. The mixture was diluted with 10 mL ether, transferred to a separatory funnel, washed 1×10 mL saturated $NH_4Cl$ solution, then extracted 3×10 mL 5% HCl solution. The acidic extracts were basified using concentrated $NH_4OH$ solution then extracted 3×15 mL ether. The organic extracts were filtered through a silica gel pad then concentrated to afford 280 mg of the free base of the desired compound as a white solid (80% yield). This material was dissolved in 5 mL ethyl acetate. Ethyl acetate saturated with HCl (5 mL) was added. 1-Phenyl-1-(4-phenyl-piperazin-1-yl)-cyclohexane dihydrochloride (Compound 1) which precipitated out of solution (88 mg) was collected by filtration, washed with ethyl acetate and dried in vacuo.

EXAMPLE III

The following compounds were prepared essentially according to the procedure described in Examples I–II:

a) 1-(3-Methoxyphenyl)-1-(4-phenylpiperazin-1-yl)-cyclohexane dihydrochloride (Compound 2).

b) 1-(3-Methoxyphenyl)-1-[4-(2-pyrimidinyl)-piperazin-1-yl]-cyclohexane dihydrochloride (Compound 3).

c) 1-(3-Methoxyphenyl)-1-[4-(2-pyridinyl)-piperazin-1-yl]-cyclohexane dihydrochloride (Compound 4).

d) 1-(3-Methoxyphenyl)-1-[4-(2-fluorophenyl)-piperazin-1-yl]-cyclohexane dihydrochloride (Compound 5).

e) 1-(3-Methoxyphenyl)-1-[4-(4-fluorophenyl)-piperazin-1-yl]-cyclohexane dihydrochloride (Compound 6).

f) 1-(3-Hydroxyphenyl)-1-(4-phenylpiperazin-1-yl)-cyclohexane dihydrochloride (Compound 7).

g) 1-(3, 5-Dimethoxyphenyl)-1-(4-phenylpiperazin-1-yl)-cyclohexane dihydrochloride (Compound 8).

h) 1-(3-Ethoxyphenyl)-1-(4-phenylpiperazin-1-yl)-cyclohexane dihydrochloride (Compound 9).

i) 1-(3-Methoxyphenyl)-1-(4-phenylpiperazin-1-yl)-4-phenyl-cyclohexane dihydrochloride (cis isomer: Compound 10, trans isomer Compound 11).

j) 1-(3-n-Butoxyphenyl)-1-(4-phenylpiperazin-1-yl)-cyclohexane dihydrochloride (Compound 12).

k) 1-(3-Methoxyphenyl)-1-(4-phenylpiperazin-1-yl)-4-methyl-cyclohexane dihydrochloride (cis isomer: Compound 13, trans isomer: Compound 14).

l) 1-(4-Methoxyphenyl)-1-(4-phenylpiperazin-1-yl)-cyclohexane dihydrochloride (Compound 15).

m) 1-(2-Methoxyphenyl)-1-(4-phenylpiperazin-1-yl)-cyclohexane dihydrochloride Compound 16).

n) 1-(3,4-Methenedioxyphenyl)-1-(4-phenylpiperazin-1-yl)cyclohexane dihydrochloride (Compound 17).

o) 1-(3-Ethoxyphenyl)-1-(4-phenylpiperazin-1-yl)-4-methyl-cyclohexane dihydrochloride (cis isomer: Compound 18, trans isomer: Compound 19).

p) 1-(3-Ethoxyphenyl)-1-(4-phenylpiperazin-1-yl)-4-ethyl-cyclohexane dihydrochloride (cis isomer: Compound 20, trans isomer: Compound 21).

q) 1-(3-Isopropoxyphenyl-1-yl)-(4-phenylpiperazin-1-yl)-4-methyl-cyclohexane dihydrochloride (cis isomer: Compound 22, trans isomer: Compound 23).

r) 1-(3-Methoxyphenyl)-1-(4-phenylpiperazin-1-yl)-3-methyl-cyclohexane dihydrochloride (cis isomer: Compound 24, trans isomer: Compound 25).

s) 1-(3-Benzyloxyphenyl)-1-(4-phenylpiperazin-1-yl)-cyclohexane dihydrochloride (Compound 26).

t) 4-(3-Ethoxyphenyl)-4-(4-phenylpiperazin-1-yl)-tetrahydropyran dihydrochloride (Compound 27).

u) 4-(3-Ethoxyphenyl)-4-(4-phenylpiperazin-1-yl)-tetrahydrothiopyran dihydrochloride (Compound 28).

v) 1-(3-Methoxymethoxyphenyl)-1-(4-phenylpiperazin-yl)-4-methyl-cyclohexane dihydrochloride (cis isomer: Compound 29, trans isomer: Compound 30).

w) 1-(3-Ethoxymethoxyphenyl)-1-(4-phenylpiperazin-1-yl)-4-methyl-cyclohexane dihydrochloride (cis isomer: Compound 31, trans isomer: Compound 32).

x) 1-(3-Ethoxyphenyl)-1-(4-phenylpiperazin-1-yl)-4-methoxy-cyclohexane dihydrochloride (cis isomer: Compound 33, trans isomer: Compound 34).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claim. To particularly point out and distinctly claim the subject matter regarded as invention, the following claims conclude this specification.

What is claimed is:

1. A compound selected from the group consisting of:

both diastereomers of 1-(3-Methoxyphenyl)-1-(4-phenylpiperazin-1-yl)-4-methyl-cyclohexane;

both diastereomers of 1-(3-Ethoxyphenyl)-1-(4-phenylpiperazin-1-yl)-4-methyl-cyclohexane;

both diastereomers of 1-(3-Ethoxyphenyl)-1-(4-phenylpiperazin-1-yl)-4-ethyl-cyclohexane;

both diastereomers of 1-(3-Isoproxyphenyl)-1-(4-phenylpiperazin-1-yl)-4-methyl-cyclohexane;

4-(3-Ethoxyphenyl)-4-(4-phenylpiperazin-1-yl)-tetrahydropyran; and 4-(3-Ethoxyphenyl)-4-(4-phenylpiperazin 1-yl)-tetrahydrothiopyran.

2. The compound of claim 1 which is both diasteromers of 1-(3-Methoxyphenyl)-1-(4-phenylpiperazin-1-yl)-4-methyl-cyclohexane.

3. The compound of claim 1 which is both diastereomers of 1-(3-Ethoxyphenyl)-1-(4-phenylpiperazin-1-yl)-4-methyl-cyclohexane.

4. The compound of claim 1 which is both diastereomers of 1-(3-Ethoxyphenyl)-1-(4-phenylpiperazin-1-yl)-4-ethyl-cyclohexane.

5. The compound of claim 1 which is both diastereomers of 1-(3-Isopropoxyphenyl)-1-(4-phenylpiperazin-1-yl)-4-methyl-cyclohexane.

6. The compound of claim 1 which is 4-(3-Ethoxyphenyl)-4-(4-phenylpiperazin-1-yl)-tetrahydropyran.

7. The compound of claim 1 which is 4-(3-Ethoxyphenyl)-4-(4-phenylpiperazin-1-yl)-tetrahydrothiopyran.

8. A pharmaceutical composition comprising an amount of a compound of claim 1 effective for inhibition of NPY1 receptors and a pharmaceutically acceptable carrier.

* * * * *

UNITED STATES PATENT AND TRADEMARK OFFICE
CERTIFICATE OF CORRECTION

PATENT NO. : 5,900,415

DATED : May 4, 1999

INVENTOR(S) : John Matthew Peterson, Charles Albert Blum, Guolin Cai, and Alan Jeffrey Hutchison It is certified that error appears in the above-identified patent and that said Letters Patent is hereby corrected as shown below:

Page 1, under [86] §371 Date and §102(e) Date "May 29, 1997" should read --April 29, 1997--

Column 3, line 67, "all" should read --alkyl--

Column 6, line 31, "all" should read --alkyl--

Column 12, line 24 "yl)cyclohexane" should read --yl)-cyclohexane--

Column 12, line 32, "q) 1-(3-Isopropoxyphenyl-1-yl)" should read -- q) 1-(3-Isopropoxyphenyl)-1-(4- --

Column 12, line 44, "(4-phenylpiperazin-yl)" should read --(4-phenylpiperazin-1-yl)-- and Column 12, line 61, "claim" should read --claims--

Signed and Sealed this

First Day of August, 2000

*Attest:*

Q. TODD DICKINSON

*Attesting Officer*     *Director of Patents and Trademarks*